United States Patent
Seth et al.

(10) Patent No.: US 9,918,622 B2
(45) Date of Patent: Mar. 20, 2018

(54) DEVICE AND METHOD FOR DETERMINING THE PRESENCE OF MIDDLE EAR FLUID

(71) Applicants: THE CLEVELAND CLINIC FOUNDATION, Cleveland, OH (US); Case Western Reserve University, Cleveland, OH (US)

(72) Inventors: Rahul Seth, Cleveland Heights, OH (US); Matthew R. Ford, Beachwood, OH (US); Andrew M. Rollins, Highland Heights, OH (US); Paul R. Krakovitz, Shaker Heights, OH (US)

(73) Assignees: The Cleveland Clinic Foundation, Cleveland, OH (US); Case Western Reserve University, Cleveland, OH (US)

( * ) Notice: Subject to any disclaimer, the term of this patent is extended or adjusted under 35 U.S.C. 154(b) by 0 days.

(21) Appl. No.: 15/596,339

(22) Filed: May 16, 2017

(65) Prior Publication Data
US 2017/0245748 A1 Aug. 31, 2017

Related U.S. Application Data

(62) Division of application No. 13/882,236, filed as application No. PCT/US2011/059311 on Nov. 4, 2011.
(Continued)

(51) Int. Cl.
*A61B 1/227* (2006.01)
*A61B 1/06* (2006.01)
(Continued)

(52) U.S. Cl.
CPC .............. *A61B 1/227* (2013.01); *A61B 1/063* (2013.01); *A61B 1/0638* (2013.01);
(Continued)

(58) Field of Classification Search
CPC ....................................................... A61B 1/227
(Continued)

(56) References Cited

U.S. PATENT DOCUMENTS 5,883,378 A * 3/1999 Irish ................. G01N 35/00871
250/214 A
6,379,969 B1 * 4/2002 Mauze ............... G01N 21/6428
422/82.05
(Continued)

FOREIGN PATENT DOCUMENTS

WO 03075761 WO A2 9/2003
WO 2009157825 WO A1 12/2009

OTHER PUBLICATIONS

The Extended European Search Report for Application No. 11838868.5, dated Apr. 22, 2015.
(Continued)

*Primary Examiner* — Anu Ramana
(74) *Attorney, Agent, or Firm* — Tarolli, Sundheim, Covell & Tummino LLP (57) ABSTRACT

A device for determining the presence of abnormal fluid in a middle ear of a subject includes an elongated probe, a first light source housed within the elongated probe, and a second light source housed within the elongated probe. The elongated probe includes a distal end for inspection of an ear. The First light source is configured to convey an optical beam through a tympanic membrane associated with the middle ear of the subject, without puncturing the tympanic membrane. The second light source is configured to convey
(Continued)

light through the distal end of the elongated probe and illuminate the tympanic membrane.

9 Claims, 6 Drawing Sheets

Related U.S. Application Data (60) Provisional application No. 61/410,114, filed on Nov. 4, 2010.

(51) Int. Cl.
*A61B 5/00* (2006.01)
*A61B 5/12* (2006.01)

(52) U.S. Cl.
CPC .......... *A61B 1/0684* (2013.01); *A61B 5/0075* (2013.01); *A61B 5/0084* (2013.01); *A61B 5/12* (2013.01); *A61B 5/6817* (2013.01)

(58) Field of Classification Search
USPC .................................................. 600/199, 200
See application file for complete search history.

(56) References Cited

U.S. PATENT DOCUMENTS

| | | | |
|---|---|---|---|
| 2002/0087084 A1 | 7/2002 | Shahar et al. | |
| 2006/0282009 A1* | 12/2006 | Oberg | A61B 5/0084 |
| | | | 600/559 |
| 2007/0112273 A1* | 5/2007 | Rogers | A61B 1/227 |
| | | | 600/475 |
| 2007/0219417 A1 | 9/2007 | Roberts et al. | |
| 2009/0185191 A1 | 7/2009 | Boppart et al. | |

OTHER PUBLICATIONS

The Supplementary European Search Report for Application No. 11838868, pp. 1-2.
The Examination Report for Application No. 11838868.5, pp. 1-3.

* cited by examiner

INNER EAR | MIDDLE EAR | OUTER EAR

DEVICE AND METHOD FOR DETERMINING THE PRESENCE OF MIDDLE EAR FLUID

CROSS-REFERENCE TO RELATED APPLICATIONS

This application is a divisional application of U.S. patent application Ser. No. 13/882,236, filed Jul. 19, 2013, which is a National Phase filing of PCT/US2011/059311, filed Nov. 4, 2011, which claims the benefit of U.S. Provisional Patent Application Ser. No. 61/410,114, filed Nov. 4, 2010 (Now Expired). The entirety of each of the aforementioned applications is hereby incorporated by reference for all purposes.

TECHNICAL FIELD

The present invention relates generally to the field of otolaryngology, and more specifically to a device and method for determining the presence of fluid in the middle ear of a subject.

BACKGROUND OF THE INVENTION

Otitis media (ear infection) is a common problem that bears significant health implications. It is the most common cause of deafness in children in the developed world, affecting up to 80% of preschool children at some time. Second only to upper respiratory infections, it is the most common indication for outpatient antibiotic use in children. Further, it is the most common reason for a child to visit the pediatrician. In the United States, the annual cost of medical and surgical treatment of otitis media is estimated at $5 billion.

Otitis media is an inflammatory and infective process affecting the middle ear and mastoid spaces. After an acute infection, there is often the development of persistent fluid within the middle ear space, known as a middle ear effusion (MEE). Persistence of a MEE can result in hearing loss and recurrent otitis media with effusion (OME). OMB is defined as the presence of a middle ear effusion for 3 months or more without gross signs of middle ear infection. However, recurrent ear infections often ensue in OME as the presence of effusion creates a fertile environment for bacterial growth.

The middle ear normally produces mucus. However, inflammatory stimuli, such as bacteria, virus, and allergy, may cause excessive production, increased viscosity, or impaired drainage of the mucus. These changes lead to mucus collection within the middle ear, forming a MEE. MEEs may persist for prolonged durations, especially in children, resulting in hearing loss and recurrent ear infections. Adults may also develop OME and persistent MEE, but are less susceptible than children in most part due to improved Eustachian tube function and position. In both adult and pediatric populations, treatment options typically include ear tube placement or close observation for resolution.

With these important clinical implications, accurate interpretation of middle ear contents proves to be au important and essential determination during the ear examination in all patients. The presence of middle ear fluid is commonly assessed by the existing technologies of otoscopy and tympanometry. However, these both have limitations in diagnostic accuracy and are dependent on the practitioner's experience, warranting consideration of alternate technologies. Tympanometry, for example, is a measure of the compliance of the tympanic membrane obtained by altering the air pressure within the ear canal and is not a true measure of the middle ear space. Therefore, the tympanometry probe placed in the external ear canal must achieve a tight seal, which is difficult to obtain in young children.

SUMMARY OF THE INVENTION

In one aspect of the present invention, a device is provided for determining the presence of abnormal fluid in a middle ear of a subject. The device includes an elongated probe, a first light source housed within the elongated probe, and a second light source housed within the elongated probe. The elongated probe includes a distal end for inspection of an ear. The first light source is configured to convey an optical beam through a tympanic membrane associated with the middle ear of the subject, without puncturing the tympanic membrane. The second light source is configured to convey light through the distal end of the elongated probe and illuminate the tympanic membrane.

Another aspect of the present invention includes a method for determining the presence of abnormal fluid in a middle ear of a subject. One step of the method comprises providing a device. The device comprises an elongated probe having a distal end, a first light source housed within the elongated probe, and a second light source housed within the elongated probe. The first light source is activated to convey an optical beam through the tympanic membrane, without puncturing the tympanic membrane. The conveyed optical beam creates a reflectance pattern associated with the tympanic membrane. Next, the reflectance pattern is observed. A substantially diffuse reflectance pattern indicates the presence of abnormal fluid in the middle ear of the subject.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

Unless otherwise defined, all technical terms used herein have the same meaning as commonly understood by one of ordinary skill in the art to which the present invention pertains.

In the context of the present invention, the term "light" can refer to electromagnetic radiation over the entire spectrum of wavelengths, such as ultraviolet, visible and infrared.

As used herein, the term "subject" can refer to any animal including, but not limited to, humans and non-human animals (e.g., non-human primates, ovines, bovines, etc.). Typically, the terms "patient" and "subject" are used interchangeably herein in reference to a human subject.

Figure 4:
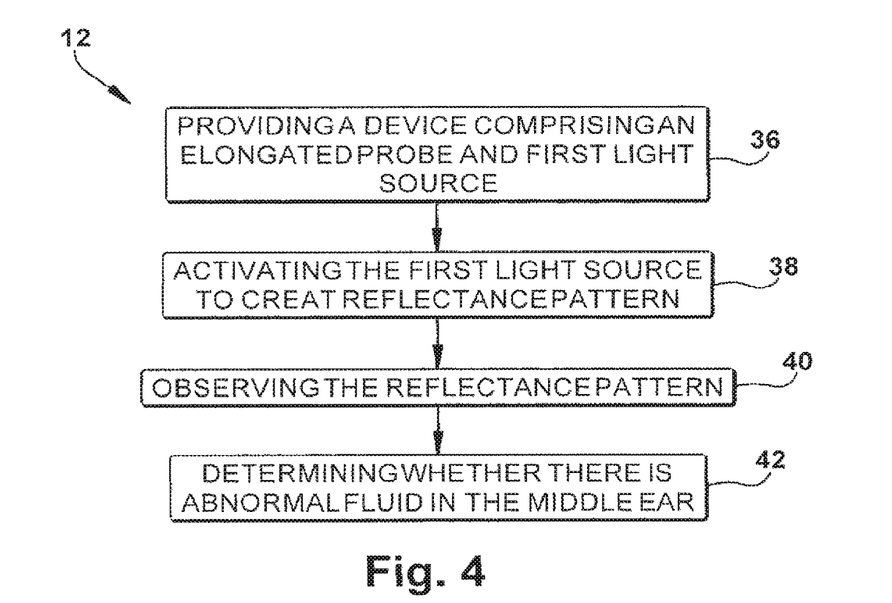
FIG. 4 is a process flow diagram illustrating a method for determining the presence of an abnormal fluid in the middle ear of a subject according to another aspect of the present invention.

The present invention relates generally to the field of otolaryngology, and more specifically to a device and method for determining the presence of fluid in the middle ear of a subject. The present invention provides a device 10 (FIG. 1) and method 12 (FIG. 4) for increasing the diagnostic abilities of conventional otoscopic devices found in most clinicians' offices, emergency departments, and clinics. The present invention is based, at least in part, on the discovery that an optical beam, such as a coherent optical beam (e.g., a low power laser) may be illuminated onto the tympanic membrane, and that the resultant reflectance pattern associated with the tympanic membrane and middle ear space is telling of whether there is abnormal fluid in the middle ear of a subject. Based on this discovery, the present invention significantly increases the diagnostic accuracy of otoscopy, which is an essential part of the physical examination performed by different practitioners in a vast number of settings (e.g., pediatricians, emergency physicians, otolaryngologists, nurse practitioners, etc.).

Existing technologies for assessing the presence of fluid in the middle ear are limited in their ease-of-use and accuracy. The present invention is based on the premise that a medical practitioner can perform otoscopy in nearly every patient with relative ease. The present invention is a simple, cost-effective, and easily interpretable addition to conventional otoscopy that provides critical information about the presence of fluid in the middle ear. As described in more detail below, the present invention eliminates the need for additional devices, testing, personnel, and computerized interpretation, thereby leading to decreased costs.

Figure 2:
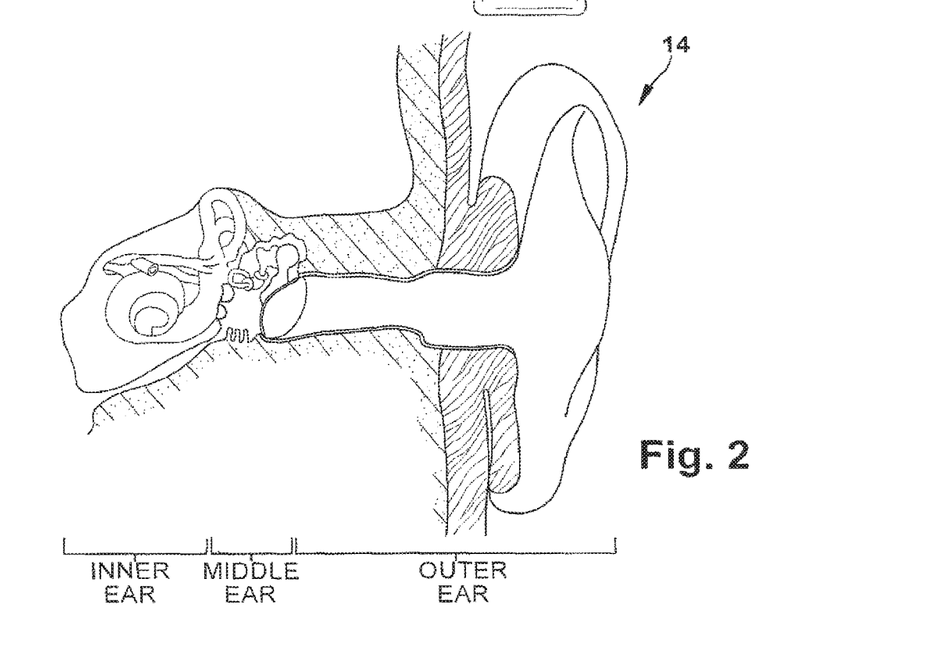
FIG. 2 is a schematic illustration showing a cross-sectional view of a human ear.

To assist the reader in understanding the relative anatomy and physiology to which the present invention pertains, a schematic illustration showing a cross-sectional view of a human ear 14 is shown in FIG. 2. There are three components to the ear 14: the outer ear; the middle ear; and the inner ear. All three are involved in hearing, but only the inner ear is responsible for balance. The outer ear is composed of the pinna, or ear lobe, and the external auditory canal. Both structures funnel sound waves towards the ear drum or tympanic membrane allowing it to vibrate. The pinna is also responsible for protecting the ear drum from damage.

The middle ear is an air-filled space located in the temporal bone of the skull. Air pressure is equalized in this space via the Eustachian tube, which drains into the nasopharynx and nose, There are three small hones, or ossicles, located adjacent the tympanic membrane. The malleus, incus, and stapes are attached like a chain to the tympanic membrane and convert sound waves that vibrate the membrane into mechanical vibrations of these three bones. The stapes fills the oval window, which is the connection to the inner ear.

The inner ear has two functions—hearing and balance. The inner ear is a warren of tubes filled with fluid and encased within the temporal bone of the skull. The bony tubes also contain a set of cell membrane-lined tubes. The bony tubes are called the bony labyrinth, which are filled with perilymph fluid, while the membranous labyrinth tubes are filed with endolymph. This is where the cells responsible for hearing are located (i.e., the hairy cells of Corti). The bony labyrinth itself has three sections: (1) the cochlea is responsible for hearing; (2) the semicircular canals have function associated with balance; and (3) the vestibule, which connects the two structures and contains two more balance and equilibrium related structures, the saccule and utricle. The final structures of the inner ear are the round window and the eighth cranial nerve (cranial nerve VIII), which is composed of the vestibular nerve and the cochlear nerve.

One aspect of the present invention includes a device (FIG. 1) for determining the presence of fluid (e.g., abnormal fluid) in the middle ear of a subject. The device 10 comprises an elongated probe 16 and a first light source 18 that is housed within the elongated probe. The elongated probe 16 is generally T-shaped and includes a distal end 20 for inspection of an ear 14, such as the auditory canal. The elongated probe 16 further includes a grip section 22 that supports a probe section 24 and an eyepiece 26, each of which extends in opposite directions. The distal end 20 of the elongated probe 16 also includes a tip 28, which can be positioned a desired distance (e.g., about 5-10 mm) from the tympanic membrane during use of the device 10.

Figure 1:
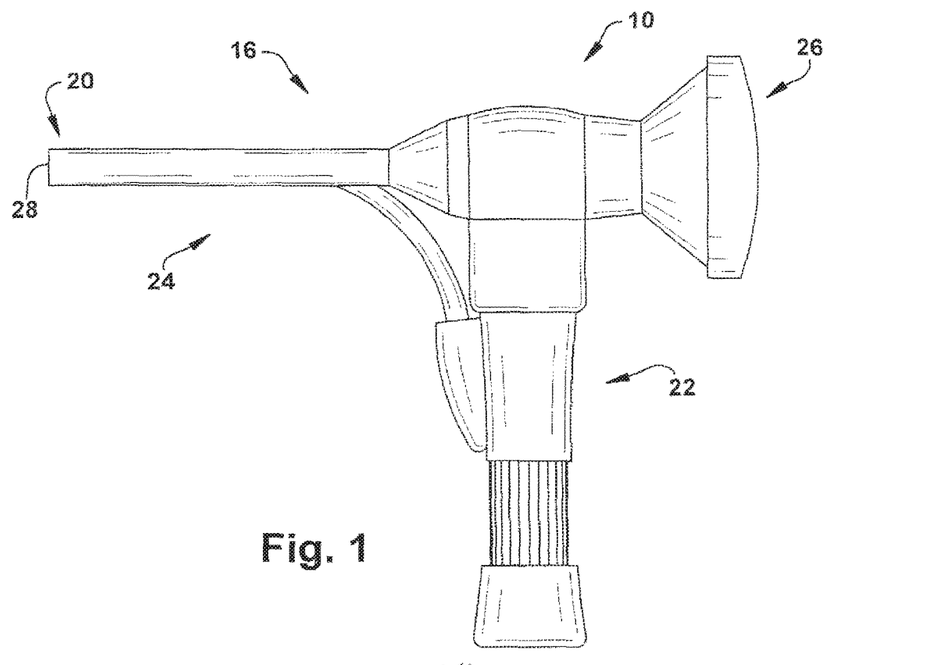
FIG. 1 is a schematic illustration showing a device for determining the presence of fluid in a middle ear of a subject constructed in accordance with one aspect of the present invention.

In another aspect of the present invention, the device 10 comprises a modified otoscope as shown in FIG. 1. Otoscopes generally consist of a handle and a head. The head can contain a light source and a simple low-power magnifying lens, typically around 8 diopters. The distal or front end of the otoscope has an attachment for disposable plastic ear specula. In one example of the present invention, the device 10 comprises a modified open otoscope. Open otoscopes are similar to conventional (closed) otoscopes, except that there is no encasing between the lens and the ear speculum. The open otoscope is often used in otolaryngology to insert instrumentation within the ear 14 (e.g., to remove ear wax under otoscopic visualization). Open otoscopes are commercially available from Welch Allyn (Skaneateles, N.Y.), for example. It will be appreciated that the otoscope can optionally comprise a conventional or closed otoscope (i.e., with encasing between the lens and the ear speculum).

Figure 3A:
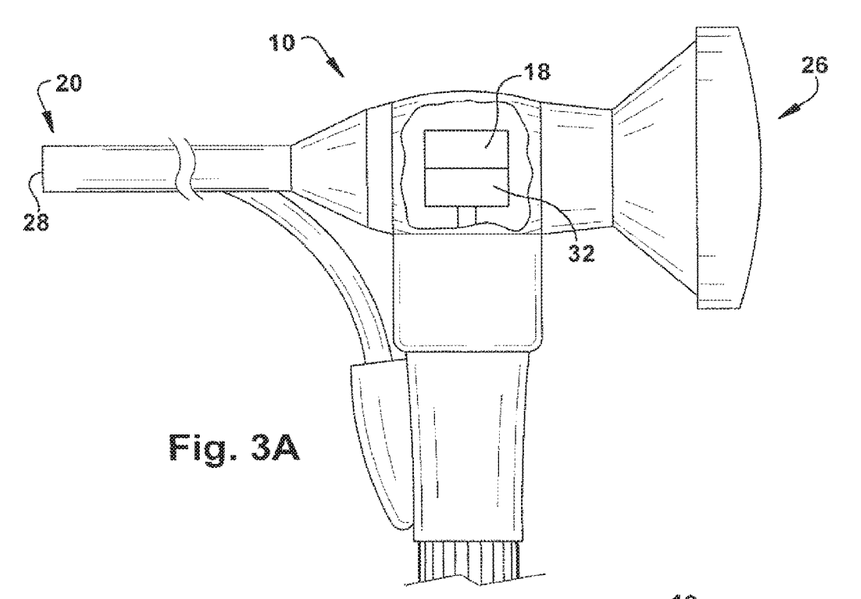
FIG. 3A is a schematic illustration showing a magnified view of first and second light sources housed within the device in FIG. 1.

As shown in FIG. 3A, the device 10 is modified to include a first light source 18 configured to convey an optical beam 30 (FIG. 5B) through a tympanic membrane associated with a middle ear of a subject. The device 10 (FIG. 3A) can additionally or optionally include a second light source 32 that is housed therein and configured to convey light through the distal end 20 of the elongated probe 16, thereby illuminating the tympanic membrane of the subject. In one example of the present invention, the second light source 32 can comprise an incandescent light. The second light source 32 can be operably connected to a dimmer switch (not shown), which allows the intensity of the second light source to be modulated (e.g., decreased) during use of the device 10.

The first light source 18 and/or the second light source 32 can be in electrical communication with the same or different power source(s) (not shown). For example, the first light source 18 and the second light source 32 can be in electrical communication with a single battery housed within the device 10. As described in more detail below, this configuration is possible because the first light source 18 only requires low power to operate. It will be appreciated that other sources of power, such as external batteries and/or power outlets, may also be used to provide energy to the first and second light sources 18 and 32.

Figure 5A:
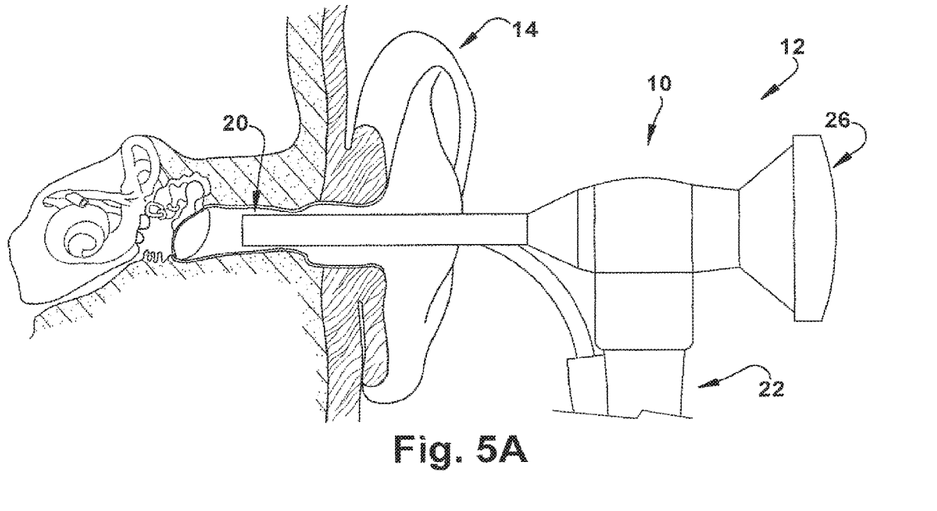
FIG. 5A is a schematic illustration showing the device of FIG. 1 inserted into the ear of a subject.
Figure 5B:
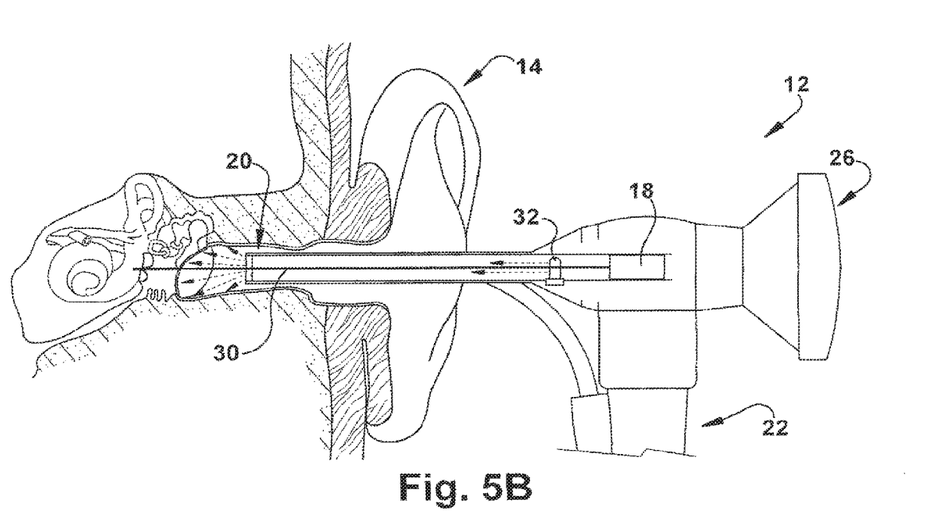
FIG. 5B is a schematic illustration showing activation of the first and second light sources in FIG. 1.

The first light source 18 can be a lower power source of the optical beam 30 (e.g., an ANSI Class IIIR device) (FIG. 5B). For example, the first light source 18 (FIG. 3A) can operate at a power of less than about 10 mW. In another example, the first light source 18 can operate at a power of less than about 5 mW. In a further example, the first light source 18 can operate at a power of greater than about 1 mW but less than about 5 mW. Advantageously, low power operation of the first light source 18 allows the optical beam 30 (FIG. 5B) to be conveyed through the tympanic membrane without puncturing or disrupting the tympanic membrane. This is unlike otoscopes used during myringotorny procedures, in which a high power coherent optical beam (e.g., a laser) is used to pierce the tympanic membrane and create a tiny incision therein.

The first light source 18 (FIG. 3A) is configured to deliver an optical beam 30 (FIG. 5B) of light. For example, the first light source 18 (FIG. 3A) can be a laser that is configured to deliver a collimated or focused optical beam 30 (FIG. 5B) having one or more wavelengths in the visible spectrum. In one example of the present invention, the first light source 18 (FIG. 3A) is configured to deliver a coherent optical beam 30 (FIG. 5B) having a wavelength of about 532 nm. In another example of the present invention, the first light source 18 (FIG. 3A) is configured to deliver a coherent optical beam 30 (FIG. 5B) having a wavelength of about 635 nm. A variety of known electromechanical devices may be used as the first light source 18 (FIG. 3A), such as light emitting diodes (LEDs), lasers and laser diodes. For example, the first source 18 can comprise a low power laser diode configured to convey a coherent optical beam 30 (FIG. 5B) having a wavelength of about 532 nm or about 635 nm.

Figure 3B:
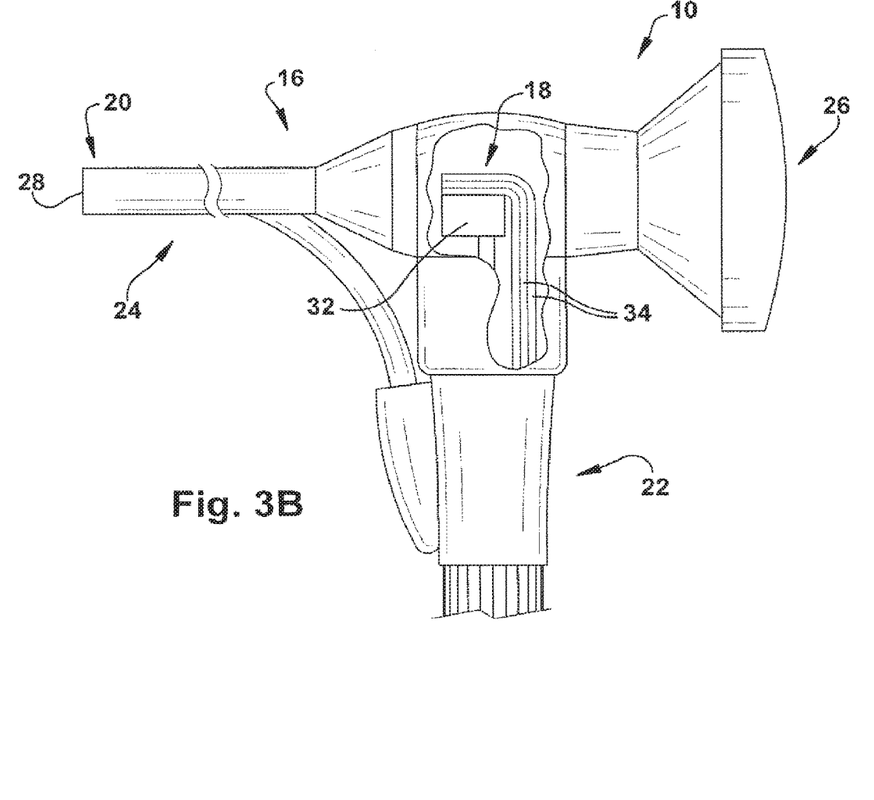
FIG. 3B is a schematic illustration showing an alternative configuration of the first light source in FIG. 3A.

It will be appreciated that first light source 18 (e.g., diode) (FIG. 3A) can be housed within the grip section 22 of the device 10. In this case, the optical beam 30 (FIG. 5B) can be propagated through one or more optical fibers 34 (e.g., optic cable(s) or light pipe(s)) (FIG. 3B) that extend from the first light source 18 through the device 10 to the distal end 20 and/or the tip 28. Although not shown, it will also be appreciated that the device 10 of the present invention can include additional components and features to optimize certain functions thereof. For example, the device 10 can include crossed polarizers to reduce the visibility of reflected light, an occluding mechanism configured to remove reflected light from the field of view, and/or color filters to improve visibility and contrast.

Another aspect of the present invention includes a method (FIG. 4) for determining the presence of fluid (e.g., abnormal fluid) in the middle ear of a subject. In one example of the present invention, the method 12 can be used to determine the presence of MEE in a subject. After an acute ear infection, there is often the development of persistent fluid within the middle ear space, which is known as MEE. Persistence of MEE poses significant health problems of conductive hearing loss leading to speech and learning delays and recurrent OME. Therefore, correct diagnosis is paramount. The most commonly used diagnostic methods include otoscopy and tympanometry; however, these methods have shown only limited accuracy and are dependent on practitioner experience, leading to frequently incorrect diagnoses, unnecessary use of antibiotics, and prolonged hearing loss. As described below, the present invention provides a simple and effective way for medical practitioners to detect abnormal fluid in the middle ear, such as MEE and thereby correctly diagnose and treat the patient.

Step 36 of the method includes providing a device 10 that is identically or similarly constructed as the device shown in FIG. 1 and described above. For example, the device 10 can comprise a modified open otoscope having a distal end 20, a grip section 22, a first light source 18 configured to convey an optical beam 30, and a second light source 32 configured to convey light through the distal end. The first light source 18 can comprise a low power (e.g., less than about 5 mW) diode (e.g., laser diode) configured to convey a coherent optical beam 30 having a wavelength of about 532 nm or about 635 nm.

The device 10 can then be positioned as shown in FIG. 5A. For example, the distal end 20 of the device 10 can be inserted into the auditory canal and then progressively advanced until the tip 28 is positioned adjacent the tympanic membrane. The tip 28 can be positioned adjacent the tympanic membrane at a desired distance, as determined by the medical practitioner. For example, the tip 28 can be positioned about 5-10 mm from the tympanic membrane. During positioning of the distal end 20, the second light source 32 (e.g., an incandescent light source) can be optionally activated to illuminate the auditory canal and the tympanic membrane.

Figures 6A, 6B:
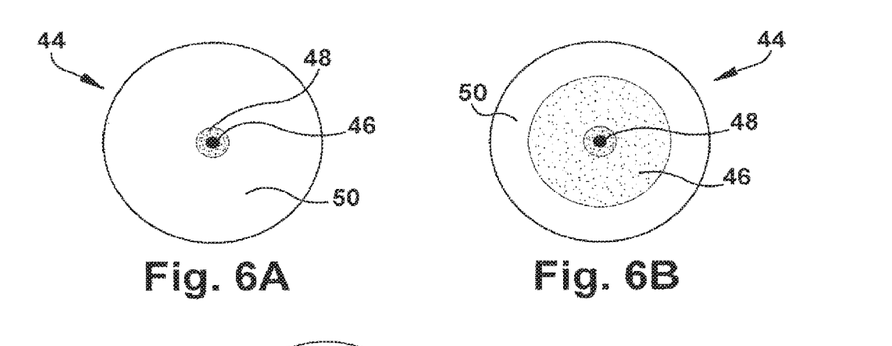
FIG. 6A is a schematic illustration showing a reflectance pattern associated with a tympanic membrane that indicates the absence of fluid in the middle ear of a subject.
FIG. 6B is a schematic illustration showing a reflectance pattern associated with a tympanic membrane that indicates the presence of abnormal fluid in the middle ear of a subject.

After the distal end 20 of the device 10 is appropriately positioned in the auditory canal of the subject, the first light source 18 is activated at Step 38 (FIG. 5B). If it has not been done so already, the second light source 32 can also be activated at Step 38. The first light source 18 can be activated by a controller (not shown) (e.g., a button) located on the device 10. Activation of the controller can cause the first light source 18 to convey an optical beam 30 through the tympanic membrane, but without puncturing or piercing the tympanic membrane. When the optical beam 30 passes through the tympanic membrane, it is reflected back onto the tympanic membrane to create reflectance pattern 44 associated with the tympanic membrane, which can be a substantially concentrated reflectance pattern (FIG. 6A) or a substantially diffuse reflectance pattern (FIG. 6B).

A reflectance pattern associated with a tympanic membrane can refer to light reflected from the tympanic membrane, as well as diffuse reflectance of light that is effused through the tympanic membrane (e.g., reflected from anything in the middle ear space). It will be appreciated that internal reflections in the tympanic membrane can contribute to the reflectance pattern, as well as tympanic membrane surface reflections. As shown in FIGS. 6A-B, the reflectance pattern 44 comprises at least two regions. A first region 46 of the reflectance pattern 44 is defined by a portion of the incident light or spot beam of the optical beam 30 reflected from the exterior surface of the tympanic membrane. A second region 48 corresponds to the remaining portion of the incident light or spot beam of the optical beam 30 that is reflected from the rear wall and/or fluid in the middle ear back toward the tympanic membrane and effuses through the tympanic membrane. A third region 50 includes a portion of the tympanic membrane that is neither transmissive nor reflective of any portion of the optical beam 30.

Alternatively, the reflectance pattern 44 can refer to the observed pattern comprising the sum of all light reflecting from the outer and inner surfaces of the tympanic membrane (and associated tissue), as well as the middle ear space (and all tissue and fluid present within the middle ear space). All the light that returns through the tympanic membrane is then observed by the user of the device 10.

To appreciate the nature of the reflectance pattern 44 created by the optical beam 30, it is important to appreciate the physical properties of light and the materials it traverses. Fundamentally, the middle ear of a human resembles a drum. A thin, partially translucent tympanic membrane is stretched over a cavity with mostly air space and a rear surface. Under abnormal conditions, the air space becomes filled with an effusion. Effusion fluid is characteristically variable in viscosity and transparency. Despite this, the light scattering properties of the fluid are substantially different from air. Air is usually regarded as a non-scattering medium. The fluid present in the middle ear is strongly forward scattering, but also includes significant scattering through a reasonably wide angle. This effect is similar to a headlight shining through fog.

Figure 7A:
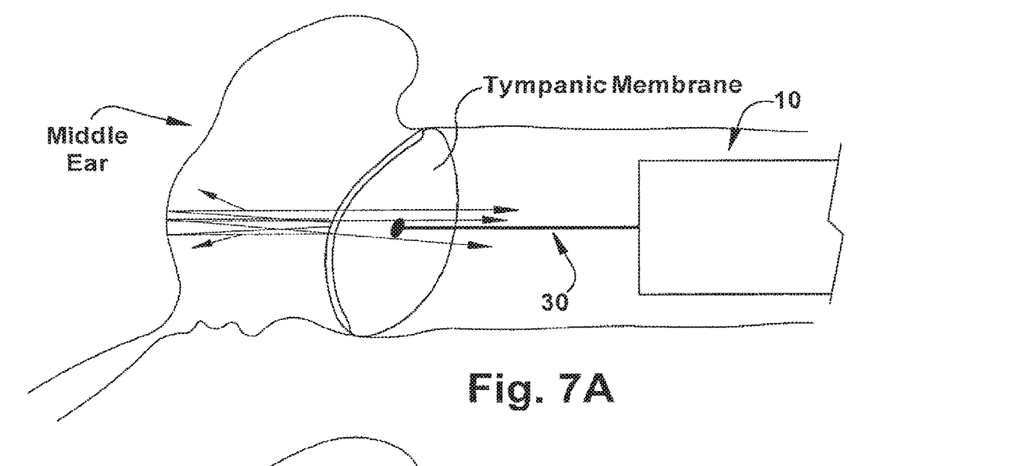
FIG. 7A is a schematic illustration showing diffuse light passing through the tympanic membrane in FIG. 6A.

In a healthy ear, the light path consists of two tissues and a total of three boundaries. Light shined into the auditory canal strikes the external surface of the tympanic membrane and then passes through this thin membrane into the middle ear space. As the light passes through the air space of the middle ear essentially unchanged, it is reflected from the irregular surface of the middle ear and returns with a slightly broader reflectance pattern 44 or reflected beam profile, which produces a substantially concentrated reflectance pattern (e.g., resembling a dot) on the surface of the tympanic membrane (FIG. 7A). As used herein, the term "concentrated reflectance pattern" can refer to effusion of light through the tympanic membrane that is substantially focused and/or narrow based the lower index of refraction of the air in the middle ear. That is, the air within a normal middle ear has a low index of refraction, such that it has very little effect on the optical beam 30 passing through the tympanic membrane (though, a certain amount may be reflected from the rear surface of the middle ear in the presence of air).

Figure 7B:
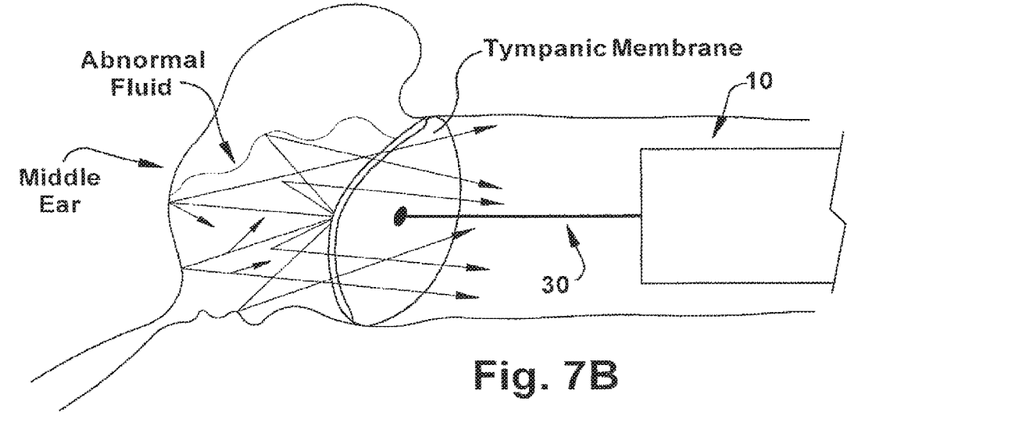
FIG. 7B is a schematic illustration showing diffuse light passing through the tympanic membrane in FIG. 6B.

In an abnormal or fluid-filled middle ear, the tympanic membrane and surrounding tissues remain largely unchanged. However, the presence of fluid drastically alters the optical effect of the middle ear. The fluid (and any scattering materials present within it, such as particulate matter and bacteria) will cause the optical beam to broaden significantly more than the air in a middle ear without fluid, thereby creating a substantially diffuse reflectance pattern on the tympanic membrane (FIG. 6B). As used herein, the term "diffuse reflectance pattern" can refer to effusion of light through the tympanic membrane that is substantially widely scattered and/or spread based on the very different optical properties of the fluid in the middle ear relative to air (e.g., while the index of refraction is different, the scattering functions of the fluid and associated particulates are also different). Therefore, a substantially diffuse reflectance pattern is such that reflected light is substantially different than the substantially concentrated reflectance pattern in terms of the observed reflectance pattern (e.g., more observed light in the substantially diffuse pattern) (FIG. 7B).

Additionally, the distance from the tympanic membrane to the tissues of the middle ear can be sufficient such that the light scattering can be perpendicular or even substantially retrograde to the original path of the optical beam 30. When light returns to the tympanic membrane, the beam is significantly broader and may result in substantially complete illumination of the tympanic membrane.

As discussed earlier, the light that creates a substantially diffuse reflectance pattern (in the presence of abnormal fluid) has a higher refractive index as compared to the light that creates a substantially concentrated reflectance pattern (in a normal middle ear). From an observer standpoint (Step 40), it will appear that the entire tympanic membrane has become illuminated with a "glow" when abnormal fluid is present. This is in stark contrast to the case of air in the middle ear, where the optical beam 30 will appear largely unchanged and appear as a substantially concentrated reflectance pattern (e.g., similar to a dot) on the tympanic membrane.

At Step 42, a determination of whether there is abnormal fluid in the middle ear is made. A substantially diffuse reflectance pattern (FIG. 6B) indicates the presence of abnormal fluid in the middle ear. For example, the presence of a substantially diffuse reflectance pattern can indicate the presence of MEE in the subject. Alternatively, a substantially concentrated reflectance pattern (FIG. 6A) indicates the presence of normal fluid (i.e., air) in the middle ear. The present invention thus provides a simple and effective method 12 for diagnosing otitis media. The method 12 offers significant cost savings by decreasing the number of false-negative diagnoses, which can lead to unnecessary use of antibiotics, increased bacterial resistance to antibiotics, and drive increase economic costs by heightening the costs associated with treating more advanced disease.

The present invention is further illustrated by the following example, which is not intended to limit the scope of potential applications of the invention.

EXAMPLE

Device Design

Initial device design centered on the addition of a laser diode module and mount to an existing open otoscope (Welch Allyn, Skaneateles Falls, N.Y.). For the purpose of the present invention, an open otoscope easily allows positioning and adjustment of a tightly focused beam. A simple mount was built and attached to the otoscope near the light source to secure the laser diode module.

This design allowed convenient replacement of the laser diode module so that different wavelengths (colors) may be tested on the same prototype. Also, the mount allowed accurate and stable positioning of the laser diode module so that the beam could be aimed through the opening of the speculum and illuminate onto the tympanic membrane surface. For purposes of this prototype, the laser diode module was attached to the mount by double-sided tape, and power was achieved via an external battery source. Power for the otoscope incandescent bulb was from a separate power supply built into the original device.

Device Testing

An ex vivo cadaver specimen was obtained with permission that included the ear, middle ear, temporal bone, middle fossa floor, Eustachian tube, and surrounding structures (Cleveland Clinic Anatomy Lab). Experiments were performed in the Cleveland Clinic Head and Neck institute Resident Training Temporal Bone Lab (Crile Building). The specimen was anchored in a temporal bone dissection apparatus, and the middle ear space was accessed via a middle cranial fossa approach. This access was necessary to insert and remove synthetic effusion substitute.

Effusions of the middle ear are predominantly composed of mucin, a large glycoprotein. A synthetic substitute for MEE or mucin is not available. Therefore we created a synthetic substitute for effusion for the purpose of proof-of concept testing. Surgilube (Fougera, Melville, N.Y.) was mixed with water to create a fluid with the color, consistency, and viscosity properties similar to native MEE. As MEE color can range from clear to pale yellow, food coloring was added to also create a pale yellow effusion substitute. This effusion was placed within the middle ear and then removed via the middle fossa approach superior to the middle ear space without damaging or perforating, the tympanic membrane.

Figure 8:
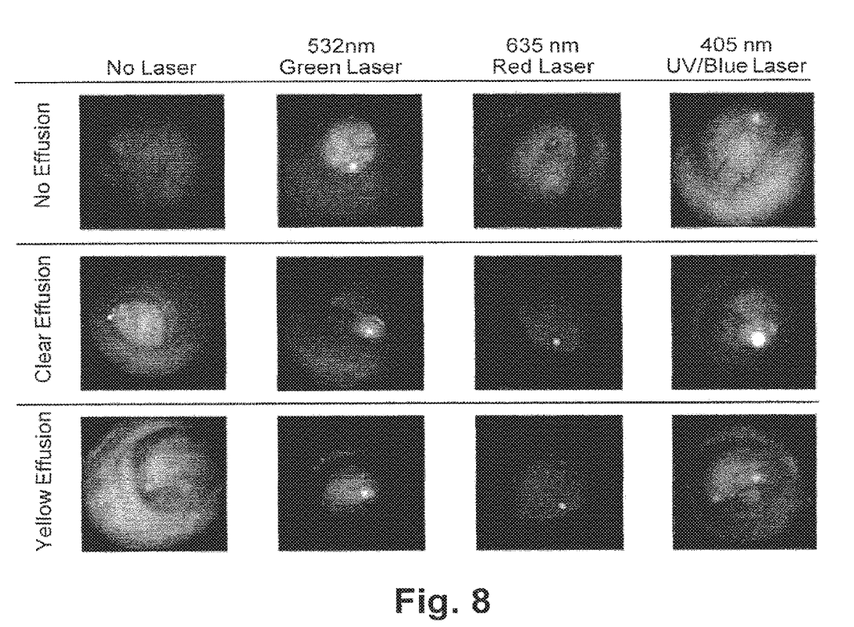
FIG. 8 is a series of photographic images showing reflectance patterns associated with a tympanic membrane without effusion, with clear effusion, and with yellow effusion using a green laser (532 nm), a red laser (635 nm), and a UV/blue laser (405 nm).

With this experimental setup, we examined the effect of laser diodes of three different wavelengths on the tympanic membrane. Green (532 nm), red (635 nm), and blue/ultraviolet (405 nm) laser colors were chosen due to their ready availability, size, visual spectrum coverage, and reasonable cost. Other colors (yellow, blue, etc.) either were of high cost (>$100) or had large modules that would not be practical for this application. Three different experimental situations of the middle ear were assessed: no fluid present; clear fluid present; and yellow-green fluid present. Visual documentation was performed with a camera, and results are shown in FIG. 8.

Photography images were obtained via the lens of the device. While the laser was engaged, the background lighting provided by the otoscope was dimmed to provide improved assessment of the laser pattern. As described previously, the laser was propagated from the device module platform through the speculum and onto the tympanic membrane. As shown in FIG. 8, the results present several important findings, including:

(1) without any laser assistance, otoscopy alone proves to be insufficient to differentiate between no effusion, clear effusion, and yellow effusion states;

(2) green (532 nm) laser-assisted visualization produces the visual effects as hypothesized. The presence of effusion is demonstrated with glow of the tympanic membrane, while when no effusion is present the laser appears as a point. This effect was demonstrated for both effusion types;

(3) red (605 nm) laser produced similar results as the green laser;

(4) blue (405 nm) laser provided expected results for the clear effusion state, but did not provide a glow fix the yellow effusion (possibly because digital (and film) cameras have significantly more sensitivity in the UV region than the human eye); and (5) while the camera provides visual documentation of the results, the extended sensitivity of the human eye over the digital camera actually provides a clearer result than the images shown in FIG. 8.

From the above description of the invention, those skilled in the art will perceive improvements, changes and modifications. Such improvements, changes, and modifications are within the skill of the art and are intended to be covered by the appended claims.

Having described the invention, the following is claimed:

1. A device for determining the presence of abnormal fluid in a middle ear of a subject, said device comprising:
   an elongated probe having a distal end configured for inspection of an ear of the subject;
   a first light source configured to convey an optical beam through a tympanic membrane associated with the middle ear of the subject, without the optical beam puncturing the tympanic membrane, said first light source being housed within said elongated probe and configured to operate at a low power,
   wherein the conveyed optical beam creates a reflectance pattern associated with the tympanic membrane that is observed through the device, wherein the reflectance pattern is indicative of whether the abnormal fluid is present in the middle ear of the subject; and
   a second light source configured to convey light through said distal end of said elongated probe and illuminate the tympanic membrane, said second light source being housed within said elongated probe and configured to operate at a low power.

2. The device of claim 1, wherein said elongated probe comprises an otoscope.

3. The device of claim 1, wherein said second light source comprises an incandescent light source.

4. The device of claim 1, wherein the low power of said first light source is less than about 10 mW.

5. The device of claim 4, wherein the low power of said first light source is less than about 5 mW.

6. The device of claim 1, wherein said first light source is selected from the group consisting of a light emitting diode (LED), a low power laser, and a low power laser diode.

7. The device of claim 1, wherein said first light source is a lower power laser diode configured to deliver a coherent optical beam having a wavelength of about 532 nm.

8. The device of claim 1, wherein said first light source is a lower power laser diode configured to deliver a coherent optical beam having a wavelength of about 635 nm.

9. The device of claim 1, wherein a substantially concentrated reflectance pattern indicates the absence of abnormal fluid in the middle ear of the subject and a substantially diffuse reflectance pattern indicates the presence of abnormal fluid in the middle ear of the subject.

* * * * *